(12) United States Patent
Dipiazza et al.

(10) Patent No.: US 7,988,838 B2
(45) Date of Patent: Aug. 2, 2011

(54) ADHESION OF MEMBRANES ON NITRIDE LAYER IN ELECTROCHEMICAL SENSORS BY ATTACHMENT TO UNDERLYING OXIDE LAYER

(75) Inventors: Frank Dipiazza, Highland, MI (US); Glenn B. Martin, Farmington, MI (US)

(73) Assignee: GE Analytical Instruments, Inc., Boulder, CO (US)

( * ) Notice: Subject to any disclaimer, the term of this patent is extended or adjusted under 35 U.S.C. 154(b) by 679 days.

(21) Appl. No.: 12/092,299

(22) PCT Filed: Nov. 1, 2006

(86) PCT No.: PCT/US2006/042809
§ 371 (c)(1),
(2), (4) Date: Jun. 12, 2008

(87) PCT Pub. No.: WO2007/053750
PCT Pub. Date: Oct. 5, 2007

(65) Prior Publication Data
US 2008/0308418 A1    Dec. 18, 2008

Related U.S. Application Data

(60) Provisional application No. 60/731,861, filed on Nov. 1, 2005.

(51) Int. Cl.
*C25B 9/10* (2006.01)
*G01N 27/333* (2006.01)
(52) U.S. Cl. ............... 204/403.06; 204/415; 205/778
(58) Field of Classification Search ......... 204/403.01–403.15, 409, 410, 204/415–419, 421, 423; 205/777.5, 778
See application file for complete search history.

(56) References Cited

U.S. PATENT DOCUMENTS

| | | | |
|---|---|---|---|
| 4,793,954 A | 12/1988 | Lee | |
| 5,102,526 A | 4/1992 | Brown | |
| 5,900,128 A * | 5/1999 | Gumbrecht et al. | 204/415 |
| 5,900,128 A | 5/1999 | Gumbrecht | |
| 6,004,442 A | 12/1999 | Choulga | |
| 6,200,444 B1 | 3/2001 | Ahlers | |
| 7,189,314 B1 | 9/2003 | Pace | |
| 6,682,649 B1 * | 1/2004 | Petersen et al. | 205/777.5 |
| 7,100,427 B2 | 5/2004 | Kahn | |
| 7,104,115 B2 | 5/2004 | Kahn | |
| 6,884,331 B1 * | 4/2005 | Van Der Wal | 204/418 |
| 7,453,254 B2 * | 11/2008 | Weber et al. | 324/71.1 |
| 2005/0181529 A1 | 8/2005 | Benzel | |
| 2005/0224346 A1 * | 10/2005 | Holm-Kennedy | 204/403.01 |

(Continued)

*Primary Examiner* — Kaj K Olsen
*Assistant Examiner* — Kourtney R Salzman
(74) *Attorney, Agent, or Firm* — GE Global Patent Operation; Catherine J. Winter

(57) ABSTRACT

An electrochemical sensor is provided that exhibits improved adhesion of the membrane to the nitride layer used as an insulating layer in silicon- or silicon-oxide-based electrochemical sensing devices. The sensing devices include a substrate, an oxide disposed on the substrate, a nitride disposed on the oxide, an electrically conductive structure disposed on the oxide layer, and an electrode disposed on the oxide layer and electrically coupled to the electrically conductive structure. At least one opening is formed in the nitride layer to form at least one adhesion trench that exposes a surface region of an oxide layer underlying the nitride layer. The membrane covers the electrode, and contacts the oxide surface regions exposed by the adhesion trenches. The contact between the membrane and the oxide surface region provides for improved adhesion of the membrane to the electrochemical sensing device.

27 Claims, 4 Drawing Sheets

U.S. PATENT DOCUMENTS

| | | |
|---|---|---|
| 2005/0251366 A1 | 11/2005 | Kahn |
| 2005/0251367 A1 | 11/2005 | Kahn |
| 2006/0020427 A1 | 1/2006 | Kahn |
| 2006/0042944 A1 | 3/2006 | Rodgers |

* cited by examiner

ADHESION OF MEMBRANES ON NITRIDE LAYER IN ELECTROCHEMICAL SENSORS BY ATTACHMENT TO UNDERLYING OXIDE LAYER

CROSS-REFERENCE TO RELATED APPLICATION

This application is related to, based upon and claims priority to U.S. Provisional Patent Application Ser. No. 60/731,861, filed Nov. 1, 2005, and entitled "Improved Adhesion of Membranes on Nitride Layer in Electrochemical Sensors by Attachment to Underlying Oxide Layer," whose entire contents (including but not limited to the specification and drawings) are incorporated herein by reference.

FIELD OF THE INVENTION

The present application relates to layer structures in electrochemical sensors and, more particularly, to structures that promote adhesion of membranes to underlying layers. The present application also relates to electrochemical sensors including ion-selective membranes.

BACKGROUND

The conventional detection of various chemical species customarily uses electrochemical sensors specially designed, e.g., for detecting the presence of the chemical species, or for determining the chemical species' concentration in a solution. Such determinations may be based on the property that, within certain limits, the potential of the electrode of the sensing device can be correlated with the chemical species' activity in the solution. The membrane of the electrochemical sensing device is selected so that the electrochemical sensors selectively measures mainly the chemical species of interest. Electrochemical sensors have many applications in the fields of medicine, engineering, industrial processing control, education, and research.

Semiconductor elements, and membrane sensors, in particular, as well as methods for producing membrane sensors on the base of semiconductor substrates such as silicon wafers are already known. Ion selective electrodes (ISE) known in the art usually comprise three common components: the internal reference electrode (typically a silver/silver chloride (Ag/AgCl)); an internal fill solution; and an organic ion selective membrane. In a conventional macro-sized ISE, a Ag/AgCl wire is used as the internal reference electrode, the internal fill solution is contained in a cylindrical plastic tube, commonly called the electrode body, an insulating barrier is provided between the internal fill solution and the sample, and the organic ion selective membrane is affixed to the end of the cylindrical tube. Importantly, the organic membrane must be affixed to form a water tight seal with the cylindrical tube, so that the electrical path is through the organic ion selective membrane. The organic membrane has to form a water tight seal with the electrode body, otherwise the voltage of the electrode is not properly measured. A water tight seal in a macro-sized ISE can be accomplished by bonding the organic membrane to the cylindrical tube, or mechanically compressing the organic membrane to the cylindrical tube.

Efforts have been made to miniaturize electrochemical sensors, and such sensors can have sensing elements with dimensions on the order of microns to less than one micron, for example. However, as ion-selective sensors are made smaller, the surface area to which the ion-selective membrane of the device adheres becomes reduced. A problem in the use of silicon nitride, or other suitable nitrides, as an insulating layer in silicon- or silicon-oxide-based electrochemical sensing devices is the difficulty in adhering encapsulants and ion-selective membranes (coatings) to the nitride. In the fabrication of silicon-based electrochemical sensing devices, electrical leads are typically patterned on a silicon oxide substrate or a silicon oxide layer on top of a silicon substrate. It is generally known that silicon oxide tends to absorb moisture and hydrate, which compromises its insulating properties. Thus, the silicon oxide is usually conformally coated with a water impermeable and electrically insulating layer, such as silicon nitride, to prevent degradation of the silicon oxide. We have found that silicon nitride is a poor surface for adhesion of ion-selective membranes in electrochemical sensing devices. The strength of the adhesion between the membrane and the nitride layer of the sensor structure can become a limiting factor in the useful life of the sensor. If the membrane adhesion is compromised, then ionic species can leak into or out of the area of the membrane that covers the reference electrode, and as a result change the voltage of the reference electrode. Furthermore, the selectivity of the signal across the membrane for the chemical species can be lost if the membrane adhesion is compromised. Therefore, the membrane should completely cover the entire active region of the electrode in order for the sensor measurements to be reliable.

The electrochemical sensing devices described herein can provide a longer useful life by virtue of increasing the adhesion strength between the membrane and the underlying layered structure of the body of the sensor.

SUMMARY

Various embodiments of the present disclosure address these as well as other concerns raised by the state of the art.

A structure in a solid-state electrochemical sensor, is provided that comprises a substrate, an oxide layer disposed on the substrate, an electrically conductive structure disposed on the oxide layer, a nitride layer disposed on the oxide layer, the nitride layer having a window therein adjacent to the electrically conducting structure, an electrode disposed at said window of the nitride layer, the electrode being electrically coupled to the electrically conductive structure, and a membrane disposed on the nitride layer, the membrane covering the electrode. The nitride layer comprises at least one opening that extends to the oxide layer, where each of the openings exposes an oxide surface region of the oxide layer, such that the membrane extends through the opening and contacts the oxide surface region.

A method of making a structure in a solid-state electrochemical sensor is also provided that comprises: forming an electrically conductive structure on an oxide layer, the oxide layer being disposed on a substrate; forming a nitride layer on said oxide layer, the nitride layer having a window therein adjacent to the electrically conducting structure, where the nitride layer comprises at least one opening that extends to the oxide layer. Each of the openings exposes an oxide surface region of the oxide layer. The method further comprises forming an electrode at the window of the nitride layer, where the electrode is electrically coupled to the electrically conductive structure; and disposing a membrane on the nitride layer. The membrane covers the electrode, such that the membrane extends through the at least one opening and contacts the oxide surface region.

In the different embodiments, the membrane may be an ion-selective membrane or a dialysis membrane. The membrane may contact both the nitride layer and the oxide surface region. Alternatively, a second oxide layer may be provided between the nitride layer and the membrane. Furthermore, the oxide surface regions may include an adhesion promoter, such as a silane or a silanol.

BRIEF DESCRIPTION OF THE DRAWINGS

The present disclosure will now be explained with reference to exemplary embodiments illustrated in the accompanying drawings to which the invention is not limited. Various advantages and other attributes of the invention will be identified or become apparent with respect to various specific embodiments, but not all embodiments within the scope of the present invention will necessarily include or have identified advantages or attributes. The scope of the invention should be determined based on recitations contained in the claims, and equivalents thereof, rather than reliance on advantages and attributes not positively recited in the claims. Further, although the term "invention" has been used in the singular, it should be recognized that more than one independent and/or distinct invention may be presented in the disclosure and claims.

DETAILED DESCRIPTION OF EXEMPLARY EMBODIMENTS

Figure 1:
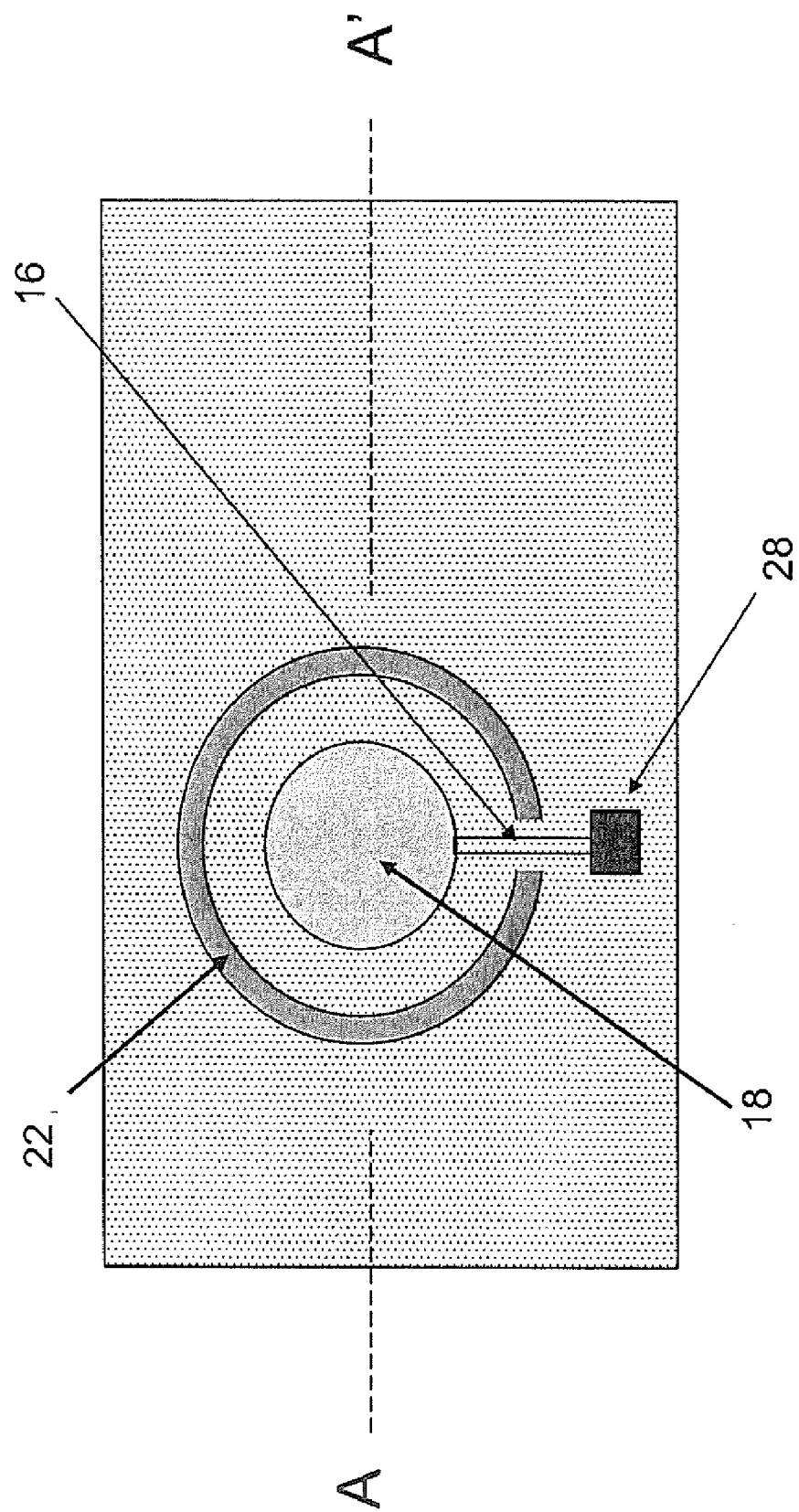
FIG. 1 shows a top view of an exemplary sensor according to an embodiment of the invention.

The fabrication of durable and robust electrochemical sensors, especially polymeric ion selective electrodes, can be technically challenging. An insulating layer can be used to insulate the underlying oxide and electrical leads, and to protect them from exposure to contaminants, such as salts and moisture, which can change their electrical properties. Therefore, an ideal insulating layer is preferably non-reactive to a broad range of chemical species. Examples of materials used to form such insulating layers include, but are not limited to, silicon nitride, silicon oxynitride, and other nitrides.

The formation of an electrochemical sensor requires adhering an encapsulant and/or a membrane onto the insulating layer (e.g., nitride layer). However, a problem of low adhesion can occur because such nitride layers exhibits very low polarity, and does not present many attachment sites for a membrane or encapsulant. We have observed that the membrane adheres much more strongly to oxides than to the insulating nitride layer.

Given that encapsulants and membranes can be made water impermeable and electrically insulating, we have observed that it is not necessary to cover the oxide with nitride where it is covered with encapsulant or a membrane. Since the membrane or encapsulant is itself an insulator, then some portions of the nitride layer may be removed without risking a short circuit due to exposure of any conductive element underlying the nitride layer, for example any electrodes or conductive interconnects. Therefore, the nitride insulating layer can be selectively patterned, e.g., selectively removed by forming trenches in the nitride layer, in order to expose corresponding surface regions of the underlying oxide from areas of the sensing device that are to be covered with a suitable membrane or encapsulant. These regions of exposed oxide provide "anchor regions" that provide for improved adhesion of the membranes or encapsulants due to the availability of covalent bonding between the membrane and the oxide. The electrochemical sensor devices described herein can provide a longer useful life by virtue of increasing the adhesion strength between the membrane and the underlying layered structure of the body of the sensor.

The descriptions provided herein with reference to membranes are also applicable to any encapsulants known in the art. An encapsulant can comprise any dielectric or insulating material that can be used for sealing, e.g., over a conductive line. As a non-limiting example, an encapsulant can be provided over an area of the device that makes connections to a circuit board. The adhesion trenches described herein in the different embodiments can be provided at any area of the device where it is sought to improve the adhesion of the encapsulant to the device.

In one embodiment, a solid-state electrochemical sensing device is disclosed herein that includes a substrate, an oxide layer disposed on the substrate, and a nitride layer disposed on the oxide layer. It will be appreciated that use of the word "on" or "between" herein does not necessarily mean that two layers are in direct contact with one another, i.e., intervening layers are not precluded. In preferred embodiments, the substrate comprises silicon, the oxide comprises silicon dioxide, and the nitride layer comprises a silicon nitride. Alternatively, the oxide may comprise a metal oxide or a semiconductor oxide, including, but not limited to, oxides of aluminum, zinc, titanium, or tantalum, or the oxide may be a glass. Alternatively, the substrate may comprise a plastic, a ceramic or a glass. The nitride layer may comprise any suitable nitride or oxynitride, such as silicon oxide or silicon oxynitride. The methods of the present application are also applicable if a perylene, polyimide, or other organic layer, or a diamond, diamond-like carbon, or other carbon-based layer replaces the nitride layers described herein. One or more electrically conductive structures can be disposed on the oxide layer, and can be disposed between the oxide layer and the nitride layer, for example. One or more openings are formed in the nitride layer that extend to the depth of the oxide layer, such that one or more surface regions of the oxide are exposed. These openings form the adhesion trenches in the electrochemical sensing device. The electrically conductive structures can be, for example, one or more conductive interconnects. One or more electrodes can be disposed on the oxide layer, and can be disposed at one or more windows formed in the nitride layer. The one or more windows can be formed adjacent to an electrically conducting structure in the device. The electrode can be electrically coupled to the electrically conductive structure. A membrane is disposed on the nitride layer such that the membrane covers the electrodes and also extends into the openings, such that the membrane contacts the exposed surface regions of the oxide layer. In some of the embodiments, the membrane contacts both the exposed surface regions of the oxide layer and the nitride layer. The adhesion trenches provided in the nitride layer serve as the anchor regions for the membrane.

The surface regions of exposed oxide provide the anchor regions for improved adhesion of the membranes or encapsulants due to the covalent bonding that can be formed between the portions of the membrane that extend through the opening, and the oxide surface regions that the membrane contacts. The strength of the covalent bonding between the membrane and the oxide depends on the type of oxide used to form the oxide layer, and on the chemical composition and rheology of the membrane solution that is deposited to form the membrane. For example, silanol groups that are usually present on the surface of the oxides of silicon, such as silicon dioxide, can help to form the covalent bonds that promote greater adhesion between the membrane and the oxide layer.

Figure 2:
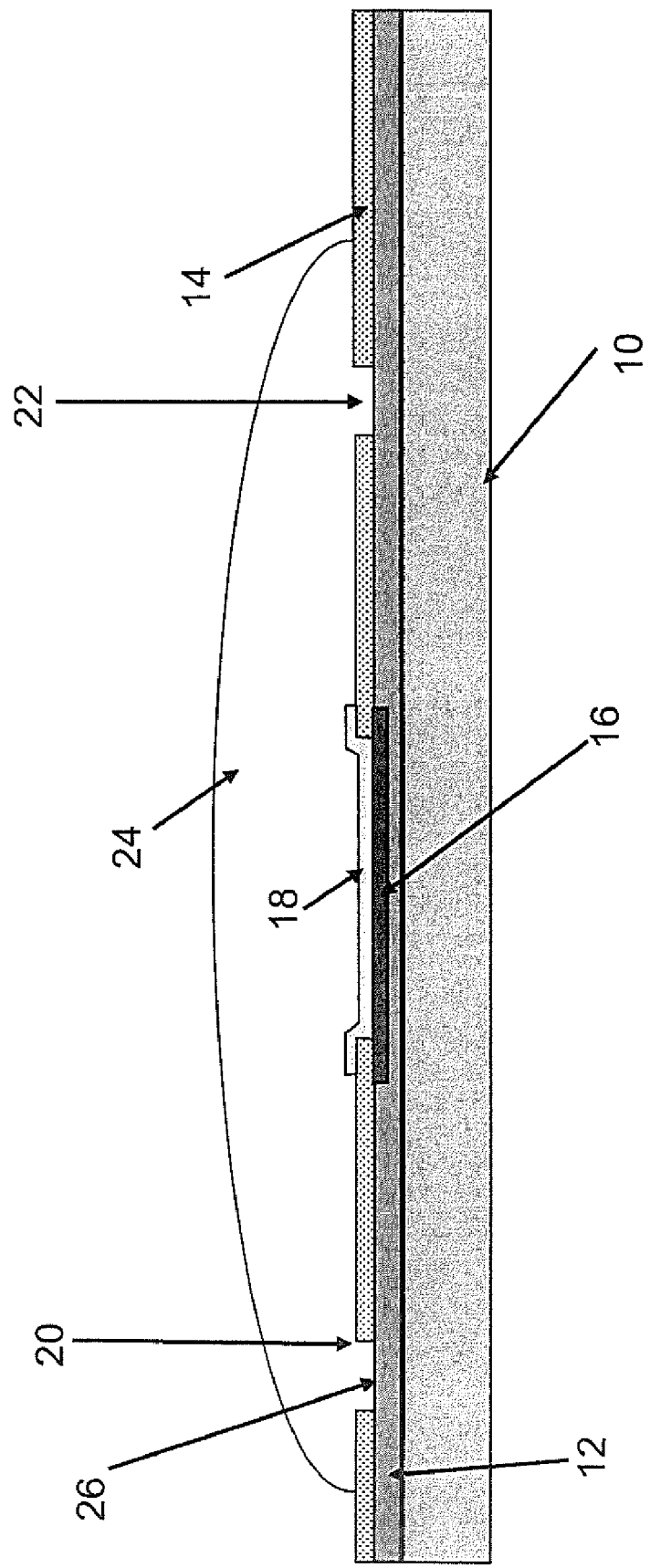
FIG. 2 illustrates a cross sectional view of the exemplary sensor along line A-A' of FIG. 1, showing the adhesion trenches formed in the nitride layer.

FIGS. 1 and 2 illustrate an exemplary configuration according to an embodiment of the invention. FIG. 2 shows a cross sectional view along the line A-A' in the top view of FIG. 1. As shown in FIG. 2, the exemplary structure comprises a substrate 10, and an oxide layer 12 disposed on the substrate. Non-limiting examples of substrate 10 include silicon, silicon oxide on silicon, ceramics, etc. It will be appreciated that a "substrate" as referred to herein may comprise multiple layers and is not limited to a bottom-most layer of a structure. Non-limiting examples of oxide layer 12 include silicon dioxide, or any other suitable type of oxide. A nitride layer 14, e.g., serving as a passivation layer, is disposed on oxide layer 12. Non-limiting examples of suitable nitrides include silicon nitride and silicon oxynitride.

As illustrated in FIGS. 1 and 2, an electrically conductive structure 16, such as, but not limited to, a platinum or other metal interconnect, is disposed between the oxide layer 12 and the nitride layer 14. Conductive structure 16 provides for an electrical connection to the electrochemical sensing device through a contact window 28. One or more electrodes 18 are provided that disposed on the oxide layer and electrically coupled to the electrically conductive structure 16. FIG. 2 illustrates electrode 18 disposed at a window formed in nitride layer 14. In the different embodiments, the one or more electrodes 18 may be electrically coupled to the electrically conductive structure 16 by being directly in contact with the electrically conductive structure 16, or the one or more electrodes 18 may be electrically coupled to the electrically conductive structure 16 through one or more intermediate structures or layers. For example, in the illustration of FIG. 2, electrode 18 is electrically coupled through being in contact with the electrically conductive structure 16. Electrodes 18 may also be in contact with the nitride layer 14, as illustrated in FIG. 2. The electrode 18 can serve as a reference electrode and can be for example silver/silver chloride, silver/silver bromide, silver/silver iodide, platinum, iridium oxide, or any other suitable electrode such as known to those of ordinary skill in the art. Suitable microelectronics deposition and patterning techniques are known to those or ordinary skill in the art and can be used to deposit and pattern the various layers. Also, suitable sputtering, evaporation, deposition and chloridization techniques are known to those of ordinary skill in the art and can be used to prepare the one or more electrodes. As illustrated in FIG. 1, the electrode 18 can be formed in the shape of a disk, or can be configured or patterned in any other suitable shape.

FIG. 2 illustrates two openings 20 that are formed in the nitride layer, and that extend to the depth of the oxide layer 12, such that surface regions 26 of the oxide layer 12 are exposed. The openings 20 form the adhesion trenches 22 in the sensing device. A membrane 24 is disposed on the nitride layer 14 such that the membrane 24 covers the electrode 18, some portions of the nitride layer 14, and also extends into the openings 20. In the preferred embodiments, the membrane 24 contacts the exposed surface regions 26 of the oxide layer 12. In some embodiments, the membrane 24 contacts both the exposed surface regions 26 of the oxide layer 12, and the nitride layer 14. The adhesion trenches 22 provided in the nitride layer 14 serve as anchor regions for membrane 24.

Methods are also described herein that provide for greater adhesion of a membrane to an electrochemical sensing device. The methods include the steps of selectively patterning (e.g., removing) portions of the nitride layer of an electrochemical sensing device from the areas of the device that are to be covered with a suitable membrane or encapsulant, in order to provide openings that expose corresponding surface regions of the underlying oxide. The openings may be formed at the time that the nitride layer is deposited on the structure using suitable masks, as known in the art. Alternatively, the openings may be formed after the nitride layer has been deposited, using a wet-etch or other technique known in the art. In preferred embodiments, the openings are adhesion trenches formed in the nitride layer that extend through to the oxide layer. The surface regions of the exposed oxide provide anchor regions for the improved adhesion of the membranes or encapsulants, mainly due to the covalent bonding that can occur between the portions of the membrane that extend through the openings and the oxide surface regions that the membrane contacts.

The openings 20 of the adhesion trenches 22, for example, those illustrated in FIGS. 1 and 2, can be formed in the nitride layer 14 using any standard patterning technique known in the art. The shape of the opening can be in the form of a narrow trench that is rectangular in cross-section and substantially circular overall in shape in plan view, and that substantially surrounds the electrode, as illustrated in FIG. 2. However, other shapes can be used for the overall shape of the adhesion trench. For examples, the overall shape of the adhesion trench in plan view can be oval-shaped, hexagonal, etc. A small region through which the adhesion trench does not extend can be provided in proximity to any electrical connection (e.g., metal interconnect line 16 illustrated in FIG. 1) to avoid having the membrane contact the electrical connection. Also, whereas only one substantially circular adhesion trench is illustrated in FIG. 1, two or more adhesion trenches, with one disposed around another, e.g., as substantially concentric circles or other concentric polygonal shapes, can be used to enhance adhesion of the membrane. The addition of more than one adhesion trench would provide a good seal even if delamination should occur at some point in one of the adhesion trenches.

Figure 3:
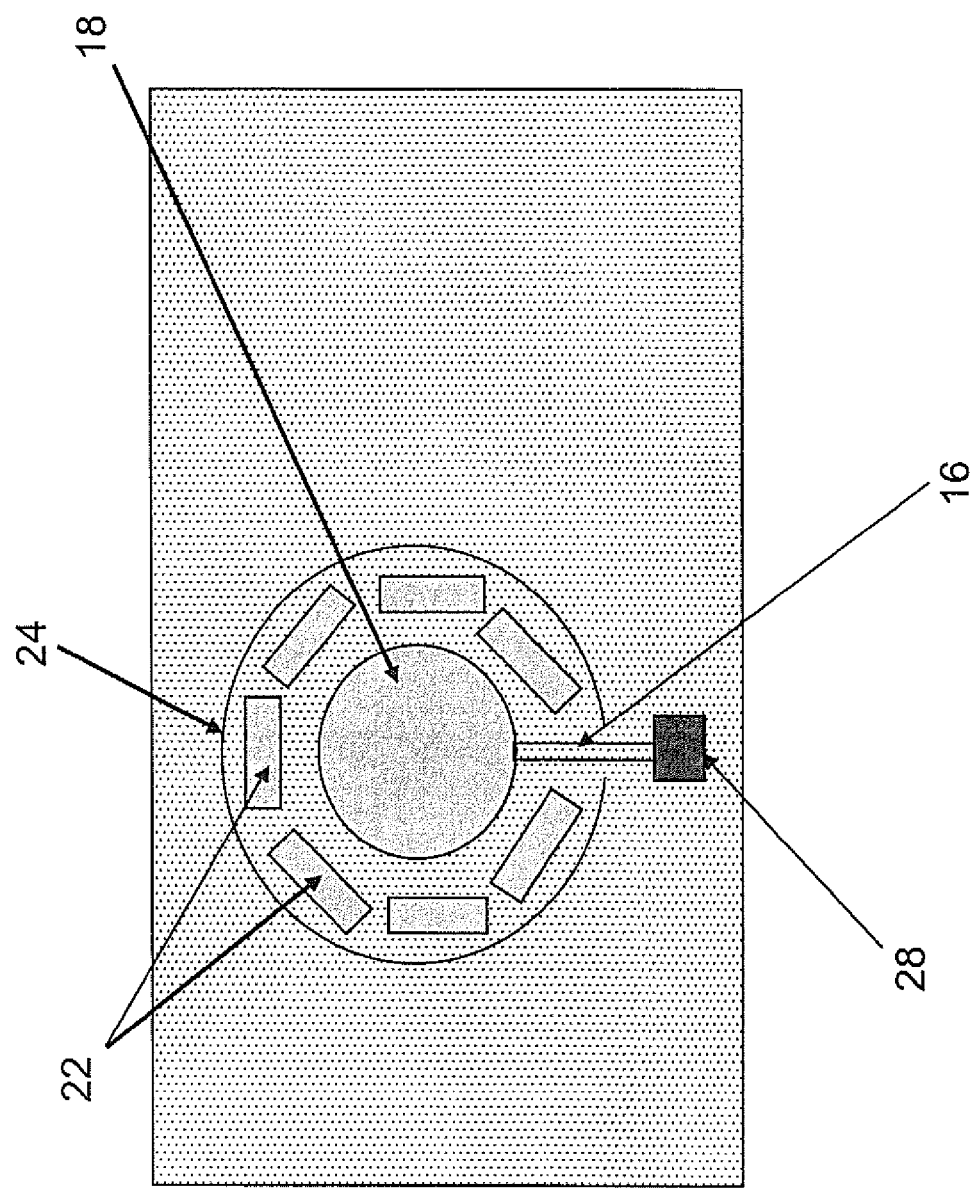
FIG. 3 shows a top view of an exemplary sensor according to another embodiment of the invention.

The strength of the adhesion between the membrane or encapsulant and the oxide surface regions varies with the total contact area between the two. Therefore, it is preferable for the adhesion trench to be as long in total length as possible, within the constraints of the total area covered by the membrane. However, the adhesion trench need not be a single continuous feature. For example, the anchor regions may be formed from a number of smaller adhesion trenches 22. As illustrated in FIG. 3, the anchor regions may include several separate adhesion trenches 22 that are positioned substantially under the membrane 24. Furthermore, in different embodiments, the adhesion trenches may have essentially the same shape, or some may be given different shapes. The shape and position of the adhesion trench could be tailored to conform to the shape of the features underlying the membrane, e.g., to avoid a short circuit of the electrodes 18.

The width of the adhesion trench in the plane of the substrate advantageously ranges from about 10 to about 300 microns. The depth of the adhesion trench can extend to the thickness of the nitride layer, which may range from about 50 to about 2,000 angstroms. However, the adhesion trench may extend even deeper into the structure, and extend into a portion of the oxide layer. The overall width, e.g., average diameter, of the adhesion trench in plan view is preferably bounded by the lateral width of the electrode and the membrane. However, the overall width may range from about 200 to about 1,000 microns.

According to another embodiment of the methods described herein for providing for greater adhesion of the membrane to the electrochemical sensing device, the nitride layer can be selectively removed in multiple locations to provide the openings for exposing the surface regions of the underlying oxide that are to be covered with a suitable membrane or encapsulant. As illustrated in the embodiment of FIG. 3, multiple adhesion trenches 22 formed with substantially rectangular openings 20 are provided in the nitride layer 14 of the sensing device. The adhesion trenches preferably extend through to the oxide layer of the device. The multiple regions of oxide surface 26 exposed by these openings 20 provide the several anchor regions for improved adhesion of the membranes or encapsulant. In this embodiment, the strength of the covalent bonding depends on the type of oxide used, and on the rheology of the membrane solution that is deposited to form the membrane 24. The rheology of the membrane solution should be such that it is capable of flowing into the multiple adhesion trenches for making the contacts with the oxide layer.

The adhesion trenches can be formed using any suitable patterning and etching techniques known to those skilled in the art (e.g., wet chemical etching, reactive ion etching, etc.), and the adhesion trenches can have vertical walls or sloped walls leading down from the opening to the exposed oxide surface region. Methods of controlling the selective etching (including directionality of etching) of nitride layers disposed on oxides layers are known in the art. In one embodiment, the adhesion trenches may extend through solely the nitride layer to expose the underlying oxide. Alternatively, the adhesion trench may extend through the nitride layer, and extend even into a portion of the oxide layer. The surface oxide region presented for adhesion of the membrane material would then include portions of the wall of the adhesion trench, as well as the base of the adhesion trench, allowing for even stronger adhesion. In another embodiment, portions of the oxide layer undercutting a portion of the nitride may also be removed (e.g., by using relatively non-directional etching during at least a final stage of the etching). In yet another embodiment, the portions of the walls of the adhesion trenches that comprise the nitride layer can be also coated with an oxide (e.g., using a subsequent patterned oxide deposition after forming the contact window in the nitride layer), thus providing for even greater adhesion along the walls of the adhesion trenches.

In another embodiment, the exposed oxide surface regions can be slightly roughened to promote adhesion between the membrane and the oxide. The oxide surface regions exposed by the openings in the nitride may be roughened as a result of the nitride removal process. Alternatively, the oxide surface region may be roughened by an additional etching, ion-implantation or other similar process. A roughened oxide surface region provides a larger surface contact area than a smoother region. Given that the adhesion between the membrane and the oxide depends on the total surface area, then the larger contact area of the rougher surface can provide for greater adhesion.

In another embodiment, an additional oxide layer can be disposed between the nitride layer and the membrane. The additional oxide layer can provide wider regions of oxides above the nitride layer for the membrane to adhere to, thus increasing the adhesion of the membrane to the electrochemical sensing device even in areas located away from the adhesion trenches. In another aspect of this embodiment, the additional oxide can be provided as a coating on the wall of the adhesion trenches, which would provide yet more anchor regions for greater membrane adhesion.

Figure 4:
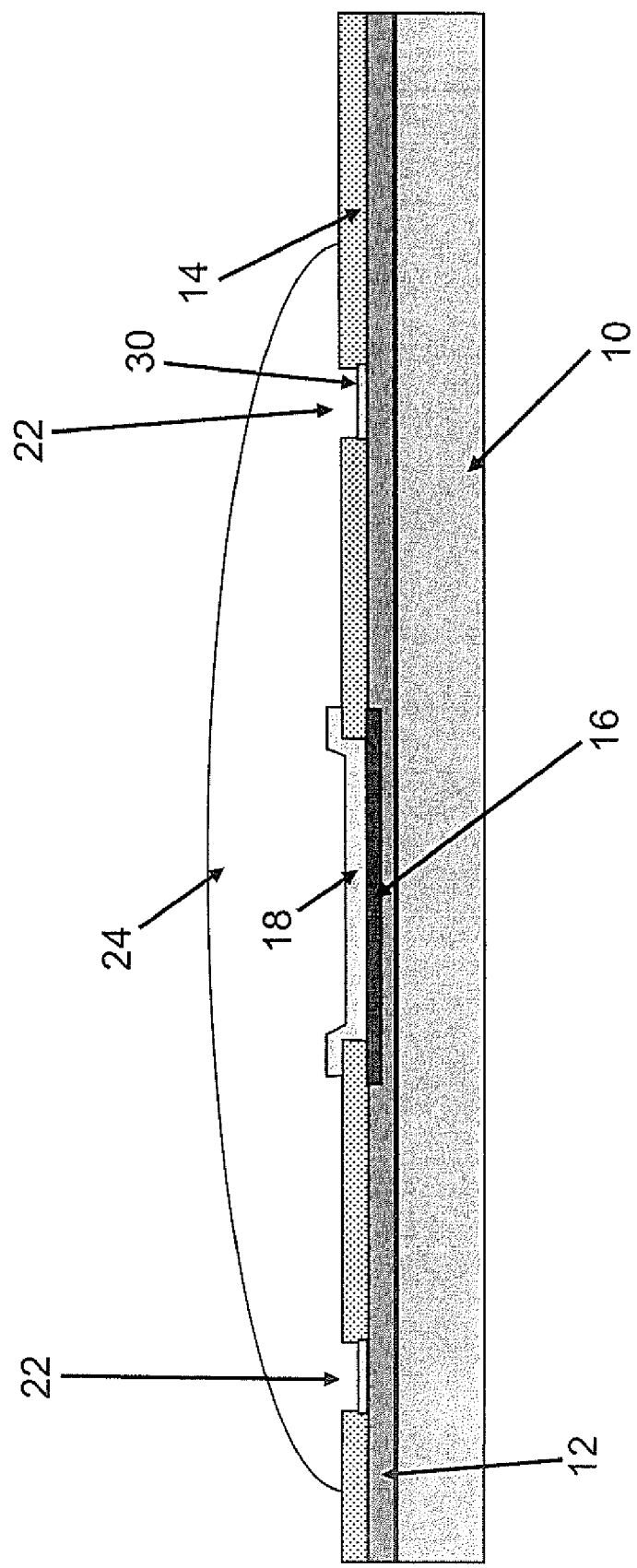
FIG. 4 illustrates another embodiment of the sensor, showing an adhesion promoter provided at the base of the adhesion trenches formed in the nitride layer.

In another embodiment, an adhesion promoter can be introduced into the adhesion trenches. The adhesion promoter can be any chemical or component that stabilizes the adhesion, or increases the strength of the adhesion, between the membrane (or encapsulant material) and the oxide surface regions. For example, an adhesion promoter can be any material that serves to increase the covalent bonding between the oxide surface regions and the membrane material. In a preferred embodiment, the adhesion promoter comprises a silane, a silanol, or other derivatives of silane or silanol. In preferred embodiments, the adhesion promoter can be provided at the oxide surface regions exposed by the opening of the adhesion trench. As the embodiment of FIG. 4 illustrates, the adhesion promoter 30 may be provided at the base of the adhesion trench 22. In preferred embodiments, the adhesion promoter can be introduced at all of the oxide surface regions that are exposed by the openings in the nitride layer. In other embodiments, the adhesion promoter can also be provided at any additional oxide layer that is disposed between the nitride layer and the membrane or encapsulant.

The adhesion promoter may be substantially unchanged by the reaction with the membrane solution when the membrane solution is applied to the sensing device. Alternatively, the adhesion promoter may be dissolved somewhat in the membrane solution or any precursor used for forming the membrane, in order to facilitate stronger adhesion of the membrane or encapsulant to the electrochemical sensing device.

Sensor Fabrication

The openings and adhesion trenches in the nitride layer of the sensing devices described herein may be formed by any method known in the art. Examples of such methods include, but are not limited to, reactive ion etching, ion-implantation, focused ion beam machining, or selective wet-etching using masks. The openings may be formed in the nitride layer after it is deposited. Alternatively, the openings and adhesion trenches may be made in the nitride layer at the time the layer is deposited through use of masks, or photolithography.

The electrochemical sensing devices disclosed herein can be manufactured using the integrated circuit fabrication technologies known in the art. Usually, integrated circuits are fabricated using a series of process steps. The system has been scale up to a mass production scale, so that thousands of circuits can be processed together at the same time in the same series of steps. The basic sensor design can be photolithographically transferred from a patterned template to a semi-conducting substrate using a photosensitive organic coating. The coating pattern is then transferred into the substrate or into a solid-state thin-film coating through an etching or deposition process. The patterned templates are in the forms of masks that can contain thousands of identical sets of patterns, and which can be used to make reproducible and inexpensive batches of sensing devices. A substrate that contains the batch of sensing devices is commonly referred to as a die. The processed die may be cleaved into several smaller segments, each containing several of the sensing device structures.

The layers of nitrides and oxides described herein are usually contained in only the uppermost portion of the substrate, down to a thickness of about 0.3 micron or so of the semiconductor substrate. Also, the lateral dimensions of the features deposited can be kept to fractions of a micron using techniques such as photoreduction. Therefore, the advantageous dimensions for the adhesion trenches described herein are achievable. Preferably, the width of the openings formed in the plane of the substrate ranges from about 10 to 300 microns. In the different embodiment, the adhesion trench described herein extends to a depth of about 50 to 2000 angstroms from the openings. Furthermore, the overall width of the adhesion trench preferably ranges from about 200 to 1000 microns in diameter or lateral spacing.

The substrates described herein may also include three-dimensional integrated circuit microstructures, formed using photolithographic techniques. The use of microfabrication to manufacture sensors produces the same benefits as it does for circuits: low cost per sensor, small size, and highly reproducible behavior. It also enables the integration of signal conditioning, compensation circuits and actuators, i.e., entire sensing and control systems, which can dramatically improve sensor performance for very little increase in cost.

The sensing device disclosed herein can be fabricated using known lithographic, dispensation and/or screen printing techniques (e.g., conventional microelectronics processing techniques). Such techniques can provide sensing devices having sensing elements with micron-sized or sub-micron-sized features, e.g., sensor elements having dimensions below 5 µm, 2 µm, 1 µm, or 0.5 µm. The sensing elements may be integrated at the chip level, and can be integrated with low-cost electronics, such as ASICs (applications specific integrated circuits). Exemplary sensors can be fabricated on silicon substrates or can be fabricated on other types of substrates such as, for example, ceramic, glass, $SiO_2$, or plastic substrates, using conventional processing techniques. Exemplary sensors can also be fabricated using combinations of such substrates situated proximate to one another. For example, a silicon substrate having some sensor components (e.g., sensing elements) can be mounted on a ceramic, $SiO_2$, glass, plastic or other type of substrate having other sensor components (e.g., other sensing elements and/or one or more reference electrodes). Conventional electronics processing techniques can be used to fabricate and interconnect such composite devices.

Other methods for manufacturing semiconductor devices that may be applicable to the sensing devices disclosed herein are known in the art, and also disclosed in U.S. Patent Publication No. 20050181529, the entire content of each of which is incorporated herein by reference.

Membrane Materials

Even though the membrane 24 in FIGS. 2 and 4 appears to be a single-layered membrane structure, the membranes disclosed herein can include either a single layer of membrane materials or may be a multi-layer membrane structure, as will be appreciated by those of ordinary skill in the art. Furthermore, in embodiments where the membrane is a multi-layer membrane structure, the different layers may each be of the same material, or one or more of the layers may include different materials. Furthermore, in the different embodiments disclosed herein, another layer of material that does not include a membrane may be interspersed between the membrane and the nitride layer.

The membrane may be any suitable ion-selective membrane known in the art. Polymeric membranes are commonly used as transducers in solid-state chemical sensors, particularly because such membranes have high selectivity to the ion of interest and can be made selective to a wide range of ions using one or many readily available ionophores. Non-limiting examples of a polymer matrix of the solid or semi-solid membrane include polyvinyls, such as polyvinyl chloride, polyvinyl stearate, polyvinyl alcohols, or polyvinyl acetate polymethacrylate, cellulose derivatives such as cellulose ester and cellulose ether, polyethylene oxides, polyethylene imines, polyamides, polyimides, polyesters, polyethers, polyphenols, polystyrenes, polyurethanes, polycarbonates, polypyrroles, polyanilines, polyacetylenes, polysiloxanes, silicon-containing polymers such as silicones, halogenated silicones or silanes, polyacroleines, polyacrylics, polyacrylates, polyacrylonitriles, polyethylenes, halogenated polymers, polyenes, polyethylene glycols, polyglycols, polyureas, polyisocyanates, polyisocyanides, polyisoprenes, polyketones, polymaleic acid (derivatives), polysaccharides, polyols, polypeptides, polyphenylene, polypropylenes, lignin or chitin. Other ion-selective membranes are known in the art, and disclosed in U.S. Pat. Nos. 6,004,442 and 6,200,444, the entire contents of each of which are incorporated herein by reference.

The membrane may be a dialysis membrane which is disposed on a film that includes a redox enzyme. Any suitable dialysis membrane known in the art may be used, including a cast polymer dialysis membrane or a cross-linked polymer dialysis membrane. Non-limiting examples of suitable dialysis membranes include: cast dialysis membranes formed from an acetone solution containing cellulose acetate and polyethylene glycol; and cross-linked polymer dialysis membranes formed from a 2-isopropanol solution containing polyethyleneimine and poly(propylene glycol) diglycidyl ether (PPGDGE). The redox enzymes can be any suitable enzyme known to one skilled in the art. Non-limiting examples of redox enzymes include glucose oxidase, latate oxidase, bilirubin oxidase, sarcosine oxidase, choline oxidase, cholesterol oxidase, and xanthine oxidase, glucose dehydrogenase, alcohol dehydrogenase, peroxidase (e.g., horseradish peroxidase) and catalase. Other suitable dialysis membranes and redox enzyme films are known in the art, and disclosed in U.S. Patent Publication No. 20060042944, the entire content of each of which is incorporated herein by reference.

Other suitable membrane materials, e.g., as used for applications other than ion-selective membranes and dialysis applications, known to those of ordinary skill in art, are also applicable to the present application.

Membrane Dispensing Techniques and Systems

A practical method for disposing the membrane on an electrochemical sensing devices with dimensions on the order of microns is to dispense the membrane solution (any other internal fill solution) onto a planar substrate that contains the electrical leads, the internal reference electrode and the insulating (nitride) barrier. For example, the membrane may be an organic ion selective membrane. The membrane is preferably affixed to the planar substrate by chemical bonding, as mechanical compression is difficult to achieve on such a small device.

The membrane or encapsulant material may be dispensed by any suitable dispensing method or system known in the art. For example, the membrane may be applied as a paste and finishing using a squeegee in a screen-printing. Alternatively, the membrane may be deposited as a membrane solution using a liquid dispensing equipment.

In a liquid dispensing method, the membrane components are dissolved in solvents to form the liquid that is applied to the sensing device. The liquid dispensing equipment could include a needle structure to dispense the membrane solution in the area of each sensing device on the die. The solvents are evaporated from the membrane solution subsequent to deposition. A major concern in such systems is how to localize the dispensed membrane liquid in the area around the electrode so that excessive overflow does not cause spread of the membrane liquid from the site of one sensing device on the die to another site. Thus, membrane design rules are influenced by the requirement of keeping membranes which are selective to different chemicals from touching. If these membranes were to touch, their ionophores could intermix, causing cross-contamination. The membrane design rules may be tailored to make allowances for such flow-out of the dispensed membrane solution after it is applied to the sensor surface, which avoids making the sensors much larger than they should be. Alternatively, the area to be occupied by the membranes may be localized through the use of barrier wells or damming walls to contain the spreading membrane liquid.

Membrane solutions optimized for a liquid dispensing method typically have low viscosities and a high solvent-to-solids ratio to keep the dispensing tip from clogging. The composition of a typical membrane solution is over 90% solvent. Care should also be taken when dispensing the low-viscosity membrane suspensions onto the sensing devices disclosed herein, in particular, to make sure that the membrane solutions extends through the openings and into the adhesion trenches in order for the membrane to contact and adhere to the exposed oxide surface regions.

For screen-printing methods, the membrane components are dissolved in solvents to form a more viscous paste that is applied to the die through a mask. Solvents and additives are selected to form the membrane paste such that the paste has an appropriate viscosity and thixotropy to achieve good pattern definition. The viscosity is also adjusted to achieve the appropriate resistance to flow from squeegee motion, and thixotropy is adjusted for appropriate resistance to secondary flow after the mask is removed from the substrate. If too little solvent is used, then a tacky, stringy paste could result that gels on the mask. On the other hand, too much solvent could result in thinner membranes with poorer pattern definition.

The print quality of the screen-printed material is also a function of mask clearance from the die or substrate, squeegee speed, squeegee shape, squeegee angle, squeegee pressure, and squeegee push-in quantity. The edge quality of the membrane pattern is determined by squeegee shape and clearance of the print mask from the substrate. Membrane pattern flow-out and thickness is determined primarily by squeegee speed, pressure, and push-in quantity. If the squeegee speed is too fast, or is accomplished without enough pressure or push-in quantity, the membrane pattern may not be completely filled with paste, the deposited material may have peaks, rather than a smooth profile, and the paste may not extend through the openings and into the trenches disclosed herein. If the squeegee speed is too slow, or the pressure and push-in quantity is too great, the pattern flow-out will increase and thickness will be decreased due the scavenging effects of the squeegee.

The screen-printing method is preferable for silicone and polyurethane membranes, as they are viscous, thixotropic pastes. In addition, several epoxies have excellent chemical compatibility with the membranes as well as good membrane adhesion and screen-printing properties.

After the membrane paste is applied to the die, it is cured, for example, by drying in the air or in an oven at elevated temperatures. The curing is controlled to avoid evaporation of the membrane components as well as solvent.

Other methods for localizing the membrane deposited in an area to prevent spread while the membrane is drying or curing are also applicable. For example, a sharp edge may be created around the area where the membrane or encapsulant is to be localized, such that the surface tension of the membrane solution prevents it from flowing at the edge. Such a sharp edge may be created by a partial etch of the nitride layer. However, in this case, the selective removal of the nitride need not progress to the extent of the underlying oxide regions. Alternatively, overflow dams may be provided on the nitride layer to localize the membrane solution to the desired area.

The rheology of the membrane or encapsulant precursor or solution should be such that air bubbles are prevented from forming in the area of the adhesion trenches. Air bubbles can decrease the adhesion strength between the membrane and the oxide. Furthermore, the air pockets left by the air bubbles tend to fill with fluid when the sensing device is immersed in a fluid sample, which can hydrate or otherwise compromise the oxide layer, and thus degrade the sensing device performance. Therefore, the viscosity of the membrane solution or precursor should be such that the material flows into and fills the adhesion trench regions.

Other methods of depositing membranes and encapsulants are also disclosed in U.S. Pat. Nos. 5,607,566 and 6,764,652, the entire contents of each of which are incorporated herein by reference. For example, the membrane may be formed using a lift-off method for patterning permselective membranes, or a solvent casting technique. Otherwise, a blank membrane solution may be coated onto regions of the die, and the membrane coating is then selectively doped over the multiple electrode sites of the sensing devices.

The electrochemical sensing devices with increased adhesion, and the methods for increasing membrane adhesion to the sensing devices, described herein are applicable to the systems and methods disclosed in copending U.S. patent application Ser. No. 10/657,760 ("Method and Apparatus for Quantitative Analysis"), and U.S. patent application Ser. No. 11/201,325 ("System and Methods for Fluid Quality Monitoring Using Portable Sensors in Connection with Supply and Service Entities"), the entire disclosures of which are incorporated herein by reference. The electrochemical sensing devices described herein are also applicable to the systems and methods disclosed in copending U.S. patent application Ser. No. 10/840,628 ("Monitoring Systems and Methods for Fluid Testing") and U.S. patent application Ser. No. 10/840, 639 ("Fluid Monitoring Systems and Methods with Data Communication to Interested Parties"), as well as U.S. Pat. No. 7,104,115 ("Fluid Treatment Apparatus with Input and Output Fluid Sensing"), U.S. Pat. No. 7,100,427 ("Multi-Sensor System for Fluid Monitoring with Selective Exposure of Sensors"), U.S. Pat. No. 4,743,954 ("Integrated Circuit for a Chemical-Selective Sensor with Voltage Output") and U.S. Pat. No. 5,102,526 ("Solid State Ion Sensor with Silicone Membrane"), the disclosures of which are incorporated herein by reference.

It should be understood that as used in the description herein and throughout the claims that follow, the meaning of "a," "an," and "the" includes plural reference unless the context clearly dictates otherwise. Also, as used in the description herein and throughout the claims that follow, the meaning of "in" includes "in" and "on" unless the context clearly dictates otherwise. Finally, as used in the description herein and throughout the claims that follow, the meanings of "and" and "or" include both the conjunctive and disjunctive and may be used interchangeably unless the context expressly dictates otherwise; the phrase "exclusive or" may be used to indicate situation where only the disjunctive meaning may apply.

The present disclosure has been explained by way of exemplary embodiments which it is not limited. Various modifications and alterations will occur to those skilled in the art without departing from the scope of the invention as articulated in the claims appended hereto and equivalents thereof.

What is claimed is:

1. A structure in a solid-state electrochemical sensor, comprising:
   a substrate;
   an oxide layer disposed on the substrate;
   an electrically conductive structure disposed on the oxide layer;
   a nitride layer disposed on the oxide layer, the nitride layer having a window therein adjacent to the electrically conducting structure;

an electrode disposed at said window of the nitride layer, the electrode being electrically coupled to the electrically conductive structure; and a membrane disposed on the nitride layer, the membrane covering the electrode, wherein the nitride layer comprises at least one opening therein extending to the oxide layer, each said opening exposing an oxide surface region of the oxide layer, such that the membrane extends through said opening and contacts said oxide surface region.

2. The structure in a solid-state electrochemical sensor of claim 1, wherein the membrane is an ion-selective membrane.

3. The structure in a solid-state electrochemical sensor of claim 1, wherein the membrane is a dialysis membrane.

4. The structure in a solid-state electrochemical sensor of claim 1, wherein the membrane comprises two or more layers of materials.

5. The structure in a solid-state electrochemical sensor of claim 4, wherein at least one of the layers of the membrane comprises ionophores, enzymes, antibodies or functional groups trapped therein.

6. The structure in a solid-state electrochemical sensor of claim 1, wherein the oxide surface region comprises an adhesion promoter.

7. The structure in a solid-state electrochemical sensor of claim 6, wherein the adhesion promoter comprises a silane.

8. The structure in a solid-state electrochemical sensor of claim 6, wherein the adhesion promoter comprises a silanol.

9. The structure in a solid-state electrochemical sensor of claim 1, wherein an oxide is disposed on the nitride layer.

10. The structure in a solid-state electrochemical sensor of claim 1, wherein the width of the opening ranges from about 10 to about 300 microns.

11. The structure in a solid-state electrochemical sensor of claim 1, wherein the at least one opening forms at least one adhesion trench in the sensor, and wherein the adhesion trench extends to a depth of about 50 to about 2000 angstroms.

12. The structure in a solid-state electrochemical sensor of claim 1, wherein the at least one opening forms an adhesion trench in the sensor, and wherein the lateral width of the adhesion trench on the structure ranges from about 200 to 1000 microns.

13. The structure in a solid-state electrochemical sensor of claim 1, wherein at least one of the openings is substantially circular, hexagonal, rectangular or oval in shape.

14. The structure in a solid-state electrochemical sensor of claim 1, wherein the electrode is a silver/silver chloride electrode, a silver/silver bromide electrode, a silver/silver iodide electrode, a platinum electrode, or an iridium oxide electrode.

15. The structure in a solid-state electrochemical sensor of claim 1, wherein the membrane contacts both the nitride layer and the oxide surface region.

16. The structure in a solid-state electrochemical sensor of claim 1, wherein a second oxide layer is disposed between the nitride layer and the membrane.

17. The structure in a solid-state electrochemical sensor of claim 16, wherein the second oxide layer comprises an adhesion promoter.

18. The structure in a solid-state electrochemical sensor of claim 17, wherein the adhesion promoter comprises a silane.

19. The structure in a solid-state electrochemical sensor of claim 17, wherein the adhesion promoter comprises a silanol.

20. A method of making a structure in a solid-state electrochemical sensor, comprising;

forming an electrically conductive structure on an oxide layer, the oxide layer being disposed on a substrate;

forming a nitride layer on said oxide layer, the nitride layer having a window therein adjacent to the electrically conducting structure, wherein the nitride layer comprises at least one opening therein extending to the oxide layer, each said opening exposing an oxide surface region of the oxide layer;

forming an electrode at the window of the nitride layer, said electrode being electrically coupled to the electrically conductive structure; and disposing a membrane on the nitride layer, the membrane covering the electrode, such that the membrane extends through said at least one opening and contacts said oxide surface region.

21. The method of claim 20, further comprising the step of providing an adhesion promoter at the oxide surface region.

22. The method of claim 21, wherein the adhesion promoter comprises a silane.

23. The method of claim 21, wherein the adhesion promoter comprises a silanol.

24. The method of claim 20, wherein the membrane contacts both the nitride layer and the oxide surface region.

25. The method of claim 20, wherein the membrane is an ion-selective membrane.

26. The method of claim 20, further comprising the step of disposing a second oxide layer is between the nitride layer and the membrane.

27. The method of claim 20, further comprising the step of providing an adhesion promoter at the second oxide layer.

* * * * *